(12) United States Patent
Ristau et al.

(10) Patent No.: US 12,226,105 B2
(45) Date of Patent: Feb. 18, 2025

(54) TENSIONABLE SURGICAL CLAMP

(71) Applicant: Institute For Cancer Research, Philadelphia, PA (US)

(72) Inventors: Benjamin T. Ristau, Philadelphia, PA (US); Robert G. Uzzo, Philadelphia, PA (US)

(73) Assignee: Institute For Cancer Research, Philadelphia, PA (US)

( * ) Notice: Subject to any disclaimer, the term of this patent is extended or adjusted under 35 U.S.C. 154(b) by 0 days.

(21) Appl. No.: 18/543,209

(22) Filed: Dec. 18, 2023

(65) Prior Publication Data
US 2024/0374263 A1  Nov. 14, 2024

Related U.S. Application Data

(63) Continuation of application No. 16/968,965, filed as application No. PCT/US2019/017609 on Feb. 12, 2019, now Pat. No. 11,944,319.

(60) Provisional application No. 62/629,470, filed on Feb. 12, 2018.

(51) Int. Cl.
*A61B 17/122* (2006.01)
*A61B 17/00* (2006.01)

(52) U.S. Cl.
CPC .. *A61B 17/122* (2013.01); *A61B 2017/00407* (2013.01); *A61B 2017/00557* (2013.01); *A61B 2017/00862* (2013.01); *A61B 2017/00964* (2013.01)

(58) Field of Classification Search
CPC ........ B42F 1/02; B42F 1/006; A61B 17/0487; A61B 17/12; A61B 17/122; A61B 2017/00407; A61B 2017/00557; A61B 2017/00862; A61B 2017/00964
See application file for complete search history.

(56) References Cited

U.S. PATENT DOCUMENTS

| | | | |
|---|---|---|---|
| 4,390,019 A | | 6/1983 | Leveen et al. |
| 5,950,283 A | * | 9/1999 | Sato ........................ B42F 1/006 24/67.5 |
| 9,446,620 B1 | * | 9/2016 | Safar ........................ B42F 1/006 |
| 11,944,319 B2 | * | 4/2024 | Ristau .................. A61B 17/122 |
| 2006/0129170 A1 | | 6/2006 | Royce et al. |
| 2009/0279718 A1 | | 11/2009 | Caploon |
| 2018/0065398 A1 | * | 3/2018 | Lim ........................ B42F 1/006 |

* cited by examiner

*Primary Examiner* — Brooke Labranche
(74) *Attorney, Agent, or Firm* — Ballard Spahr LLP

(57) ABSTRACT

The present disclosure provides surgical clamps. The clamp has a body with a mouth that opens and closes to permit the body to encircle a bundle of tissue containing a blood vessel which a surgeon wishes to occlude. The clamp also has an articulating arm that rotates on a hinge and passes through apertures of the clamp body. The apertures and/or the articulating arm include ratchet components that permit the surgeon to apply dynamic adjustable tensioning to the tissue and vessel in real time. This dynamic tension permits a surgeon to ensure a specific reduction of blood flow through the vessel.

14 Claims, 11 Drawing Sheets

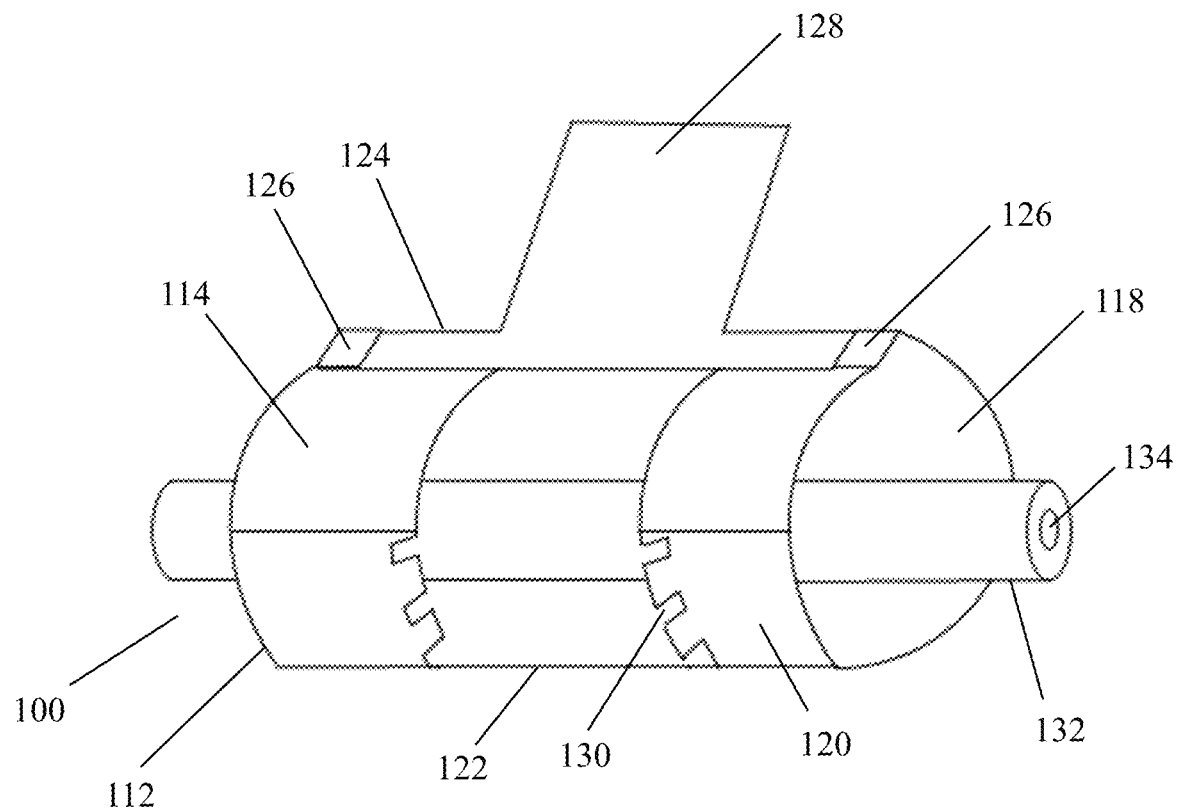
FIG. 12
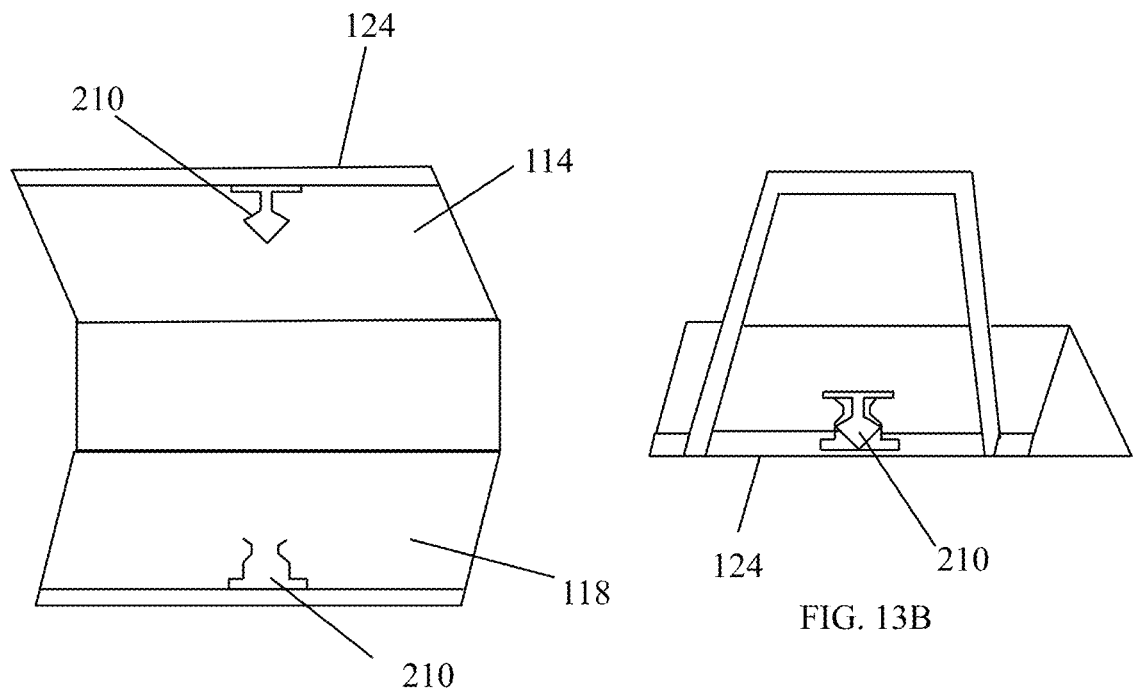
FIG. 13A
FIG. 13B

TENSIONABLE SURGICAL CLAMP

FIELD

The present disclosure is directed, in part, to the field of surgical clamps and, more specifically, to clamps with a body that encircles a blood vessel to be occluded and an articulating arm that permits adjustable tensioning of the vessel in real time to ensure specific reduction of blood flow through the vessel.

BACKGROUND

Different devices have been developed to temporarily occlude blood vessels during surgery. Surgical clamps have become an increasingly popular device of choice to accomplish this goal. Clamps are available in both large and small sizes. Larger clamps typically have shafts or handles and are most suitable for occluding larger blood vessels in surgery procedures where sufficient space is available at the surgical site. Small surgical clamps are ideal for use with smaller vessels in microvascular surgery where little space is provided.

Popular small clamps include "bulldog" clamps. "Bulldog" clamps are small clamps that are applied to a blood vessel with the thumb and forefinger or with another surgical instrument such as forceps or an applicator. Generally, bulldog clamps include two jaws attached at a pivot point. Opposite each jaw is a handle. Squeezing the handles together separates the jaws and allows the jaws to be positioned on opposite sides of a blood vessel. A spring or other biasing mechanism exists between the handles which applies a closing force to the jaws, which is transferred to the blood vessel, constricting blood flow. The clamps are then left on the blood vessel until they need to be removed.

Two known reusable "bulldog" clamps include the Acland clamp (distributed by S&T located in Switzerland) and the VAS clamp (distributed by Microsurgery Instruments, Inc. from Bellaire, Texas). Other known disposable bulldog clamps include the BEAR™ vessel clamp (Arosurgical Instruments Corporation of Newport Beach, California), the Biover microvascular clamp (distributed by Biover AG of Switzerland), and the Vascu-Statt® clamp (distributed by Scanlan International, Inc., St. Paul, MN).

Laparoscopic surgery, also called minimally invasive surgery, is a modern surgical technique involving performing surgery through a small incision in the body of a patient. Because the incision in the body is smaller than the incision made during traditional surgery, the patient may experience less pain and faster recovery times. Laparoscopic surgery presents challenges, however, associated with reduced access to the internal region of the patient where the surgery is being performed. One of these challenges in laparoscopic surgery is, sometimes, it is desirable to occlude a large blood vessel, but sufficient space is not available to use large clamps. As a result, small clamps must be used.

One surgical procedure in which space does not permit the use of large clamps to occlude large vessels, is a partial nephrectomy wherein the blood supply to a kidney is temporarily interrupted to allow a relatively hemostatic field to develop thereby enhancing visibility. Such visibility enables the surgeon to precisely remove the offending (e.g., malignant, large angiomyelolipoma, etc.) portion of the kidney. Once the tumor is removed, the surgeon repairs the resulting defect and restores blood flow to the kidney.

In a partial nephrectomy, the temporary cessation of blood flow is most frequently accomplished with a bulldog clamp device. One problem with current bulldog clamps is that they are "all or none." A surgeon places the bulldog clamp on the vessel but cannot ratchet/tension the clamp once in place. Thus, the clamp either is placed and works or it is placed and does not completely close (i.e., the clamp does not work).

A reason for such failures is that bulldog clamps suffer from numerous flaws, including being unable to apply a variable force, and applying the force unevenly to the blood vessel. Because the amount of force applied by the bulldog clamp is predetermined by the spring or biasing mechanism, a surgeon must either: (1) make do with a clamp that may apply too much force (and risk damage to the blood vessel) or too little force (and risk not adequately constricting blood flow), or (2) have many different clamps at hand to account for the need for different levels of closing force. Further, when the bulldog clamp is in the closed position, the jaws often do not apply force evenly to the blood vessel. The separation between the jaws varies along the length of the jaws, with the jaws being closer together farther from the pivot point. This risks uneven forces being applied to the blood vessel over the diameter of the blood vessel. Also, the bulldog clamp only applies force to the blood vessel from two sides, resulting in the blood vessel flattening out rather than being compressed from all sides. Accordingly, greater force is required to fully constrict blood flow, which increases the risk of damage to the blood vessel.

When the bulldog clamps fail, the surgeon is required to skeletonize the vessel to remove fat and connective tissue and then reintroduce the bulldog clamps. Such skeletonization increases the time and risk of the surgery. Furthermore, optimizing hemostasis levels leads to a smoother operation both oncologically and with regard to organ preservation.

Therefore, there exists a need for a device which can be attached to a blood vessel during surgery which can apply a variable amount of force to the blood vessel, where the force is applied to the blood vessel from multiple sides.

SUMMARY

The present disclosure provides a tensionable surgical clamp. The present disclosure relates to a surgical clamp which exhibits less (or none) of the shortcomings of bulldog clamps, such as an inability to dynamically adjust the tension applied to a large vessel to reduce or restrict blood flow through the vessel in real time, or the requirement that the vessel be skeletonized as is required at times for the bulldog clamp to work. This improved surgical clamp can be used where the surgical space does not permit the use of large clamps. In some embodiments, the disclosed clamp is an entirely intracorporeal system that may be placed in the body, opened and closed so as to encircle a bundle of tissue containing a vessel, and then ratcheted down so as to restrict or cut off the blood flow through the vessel. If desired, the clamp can be quickly released so as to reestablish blood flow through the vessel.

The disclosed clamp is comprised of: 1) a clamp body with a first surface containing a first aperture: a second surface: and a connecting surface containing a second aperture, wherein, the clamp body is resiliently biased such that the first surface and second surface contact each other at an edge: 2) a hinge at the edge of the first surface: and 3) an actuating arm rotatably secured to the first surface by the hinge. The apertures permit the actuating arm to ratchet down on the vessel by rotating through the first surface and approaching the second surface thereby compressing the vessel between the actuating arm and the second surface.

It is to be understood that both the foregoing general description and the following detailed description are exemplary, but are not restrictive, of the subject matter disclosed herein.

BRIEF DESCRIPTION OF THE DRAWINGS

The claimed subject matter is best understood from the following detailed description when read in connection with the accompanying drawings and appended claims. It is emphasized that, according to common practice, the various features of the drawing are not to scale. On the contrary, the dimensions of the various features are arbitrarily expanded or reduced for clarity. Included in the drawing are the following figures:

FIG. 12 shows a perspective view of one embodiment of the surgical clamp.

FIG. 13A shows an open-mouthed view of one embodiment of the surgical clamp.

FIG. 13B shows a latched view of one embodiment of the surgical clamp.

DESCRIPTION OF EMBODIMENTS

Figure 1:
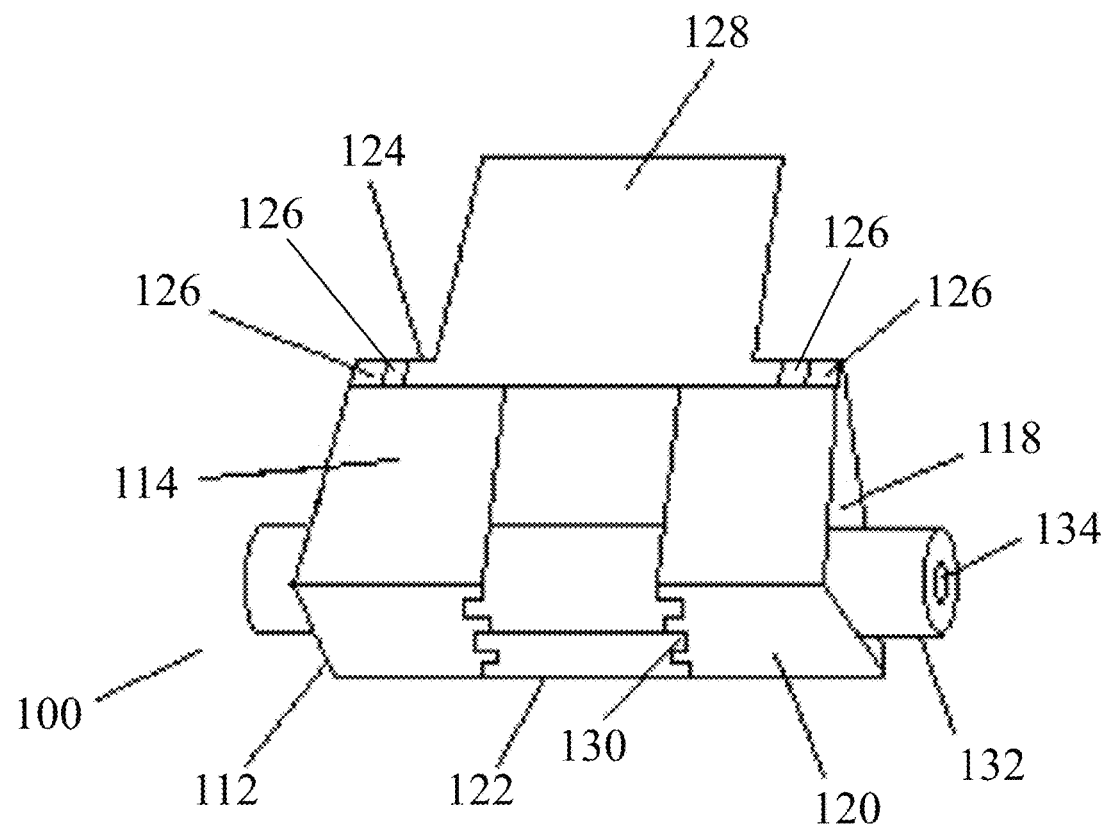
FIG. 1 shows a perspective view of one embodiment of the surgical clamp.

The terminology used herein is for the purpose of describing particular embodiments only and is not intended to be limiting.

This present disclosure provides an improved surgical clamp for occluding larger blood vessels, such as arteries or veins, when the surgical space does not permit the use of large clamps. The present disclosure includes drawings, in which like reference numbers refer to like elements throughout the various figures that comprise the drawings. In some embodiments, the disclosed clamp 100 is an entirely intracorporeal system that may be placed in the body, opened and closed so that the clamp body 112 encases a bundle of tissue 132 containing a vessel 134 and then ratcheted down using an actuating arm 128 rotatably secured to a first surface 114 by a hinge 126 so as to compress the bundle of tissue 132 containing the vessel 134 between the actuating arm 128 and a second surface 118.

In some embodiments, the clamp body 112 contains a minimum of three surfaces: a first surface 114 connected to a second surface 118 by a connecting surface 120. The three surfaces create a clamp body 112 that is substantially triangular in shape. In some embodiments, the clamp body 112 and/or the connecting surface 120 is resiliently biased such that when it is not subject to any external forces, the first surface 114 and the second surface 118 contact each other at an edge 124.

The first surface 114 and the second surface 118 of the clamp body 112 may further include a latching mechanism 210. This latching mechanism 210 permits a user to temporarily secure the first surface 114 to the second surface 118 at the edge 124 as demonstrated in FIG. 2B and FIG. 13B. The latching mechanism 210 can be used in conjunction with or in place of the clamp body 112 being resiliently biased. Furthermore, the latching mechanism 210 can automatically latch without the user's intervention or can require the active intervention of the user to engage or disengage the latching mechanism 210.

Although the clamp body 112 is made up of three surfaces, a clamp body 112 comprised of more than three surfaces is envisioned. For example, the clamp body 112 can include four surfaces in a square/rectangular/diamond configuration as disclosed in FIGS. 7C and 7D. The clamp body 112 can also include six surfaces in a hexagon configuration as disclosed in FIGS. 7A and 7B. Furthermore, the surfaces need not be flat, but may be curved. Thus, the clamp body 112, with a closed mouth, can take on enclosed shapes that are substantially circular in shape or oval shaped.

Figure 4:
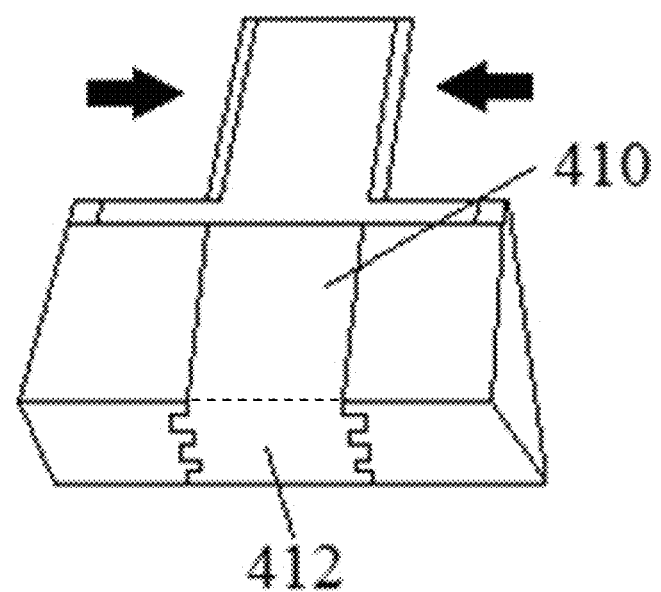
FIG. 4 shows a perspective view of one embodiment of the surgical clamp with the actuating arm under compression.
Figure 5:
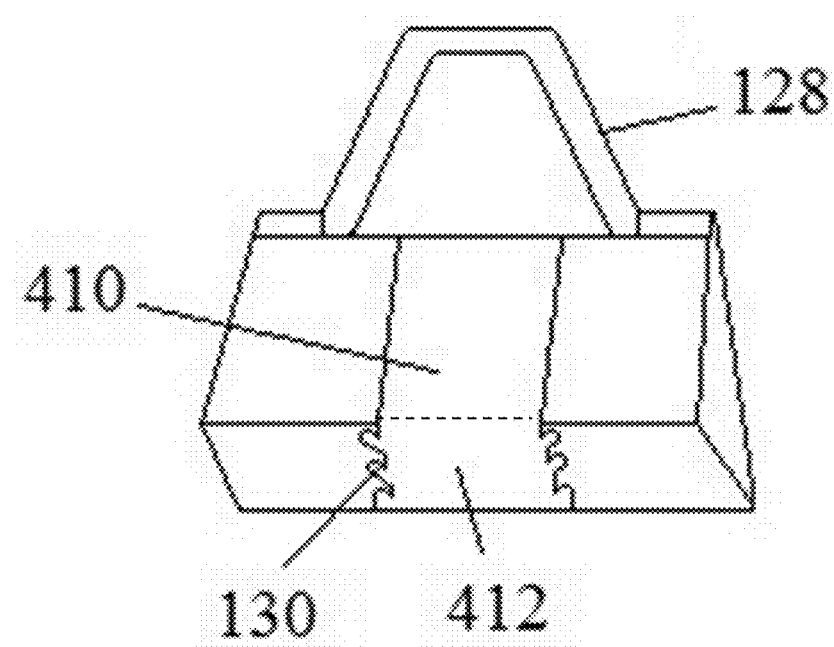
FIG. 5 shows a perspective view of one embodiment of the surgical clamp with a wire for an actuating arm.
Figure 6:
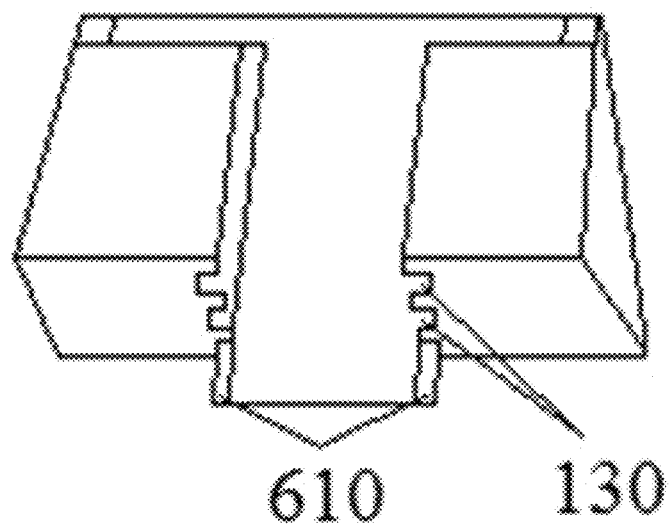
FIG. 6 shows a perspective view of one embodiment of the surgical clamp with the actuating arm rotated to into the fully closed position.

In some embodiments, the hinge 126 is attached to the first surface 114 at the edge 124 where the first surface 114 and the second surface 118 contact each other. The hinge 126 connects the first surface 114 to the actuating arm 128 but does not limit the angle of rotation between the actuating arm 128 and the first surface 114. Indeed, it is the second surface 118 that limits the rotation of the actuating arm 128 as the bundle of tissue 132, which includes the vessel 134, is compressed between the actuating arm 128 and the second surface 118. In some embodiments, the hinge 126 does not prohibit the actuating arm 128 from moving in a direction substantially perpendicular to the axis of rotation, as depicted in FIG. 4. For example, the actuating arm 128 may be wider than a first aperture 410 located in the first surface 114. The hinge 126 may permit the actuating arm 128 to be compressed, however, so as to reduce its width so that it may pass through the first aperture 410 and move forward to compress the tissue bundle 132 as depicted in FIG. 6.

There may be more than one hinge 126 on the first surface 114. Furthermore, a hinge 126 may be attached to the second surface 118 so as to permit a second actuating arm 714 to be rotatably attached to the second surface 118.

Figure 2A:
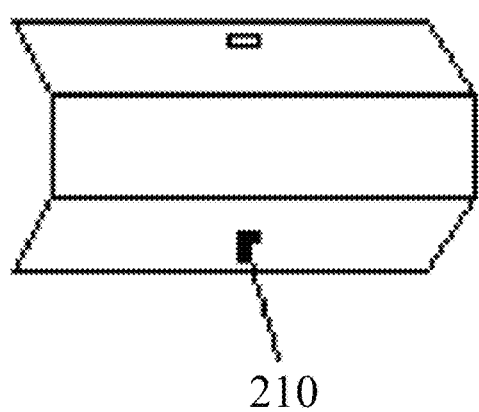
FIG. 2A shows an open-mouthed view of one embodiment of the surgical clamp.
Figure 2B:
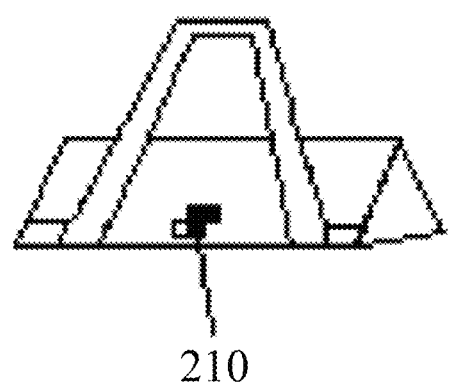
FIG. 2B shows a latched view of one embodiment of the surgical clamp.
Figure 3:
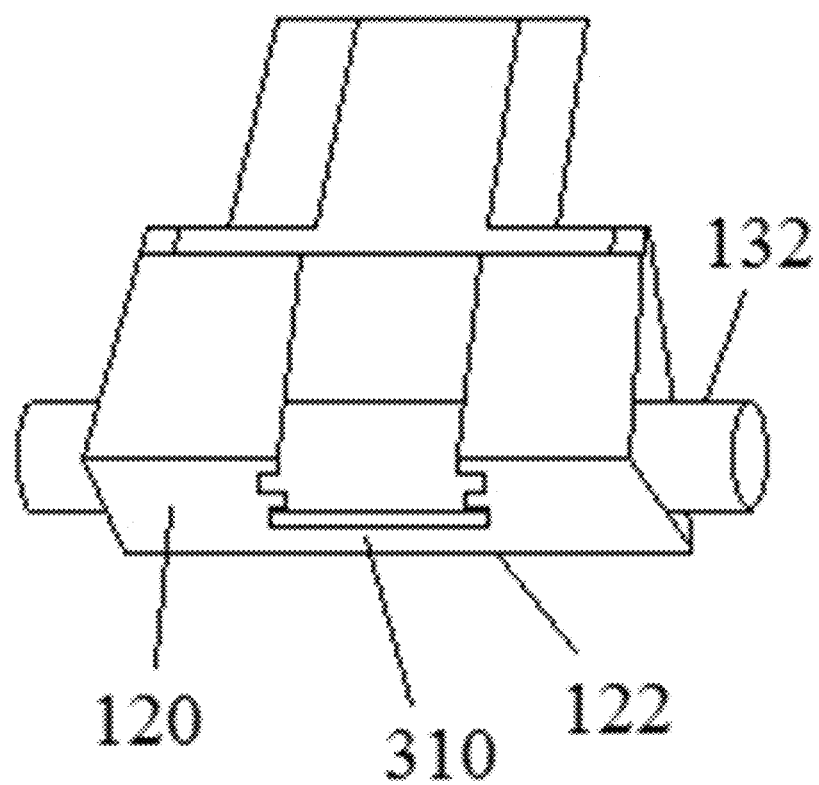
FIG. 3 shows a perspective view of one embodiment of the surgical clamp with a lip.
Figure 7A:
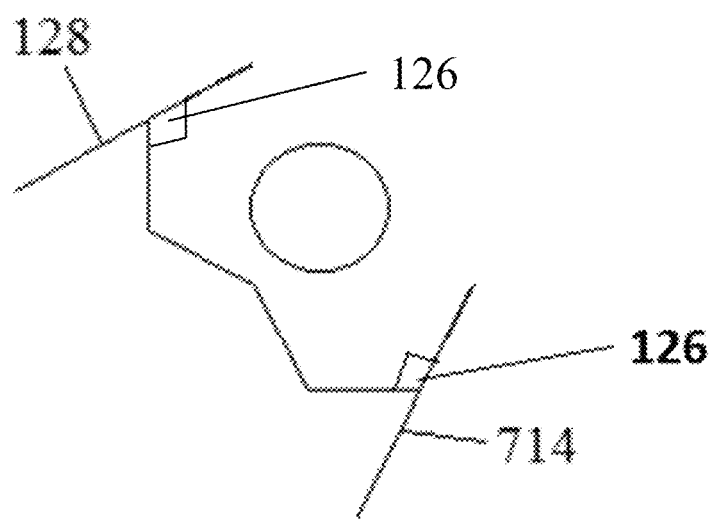
FIG. 7A shows a side view of one six-sided embodiment of the surgical clamp including two actuating arms with the mouth open.
Figure 7B:
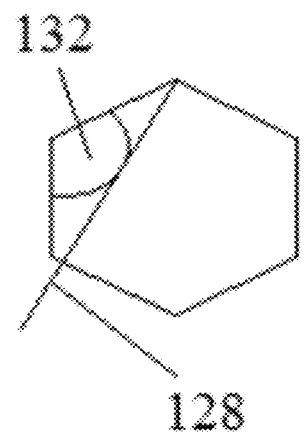
FIG. 7B shows a side view of one six-sided embodiment of the surgical clamp where the mouth is closed and the vessel is being compressed.
Figure 7C:
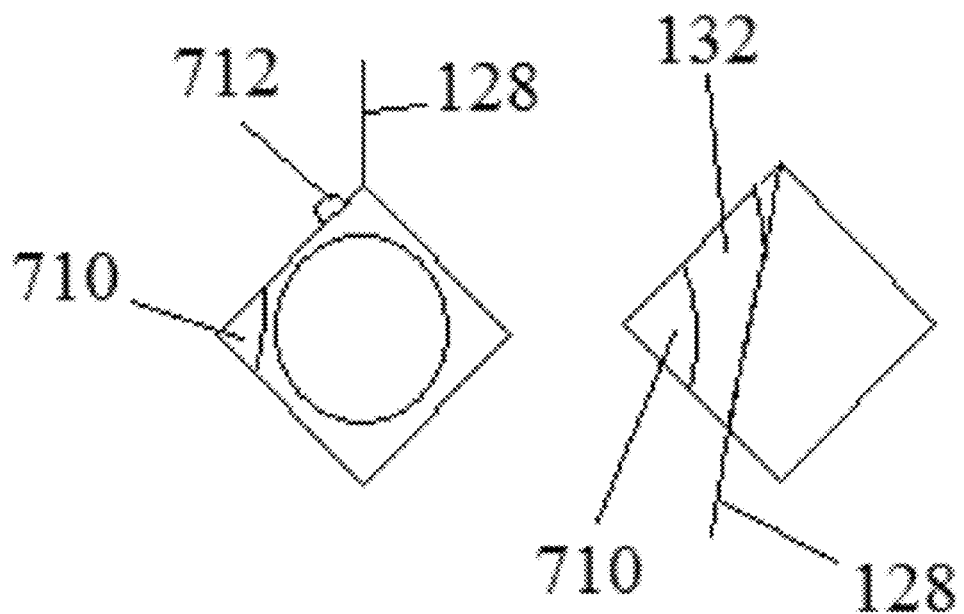
FIG. 7C shows a side view of one four-sided embodiment of the surgical clamp with a balloon and anchor point depicted.

By applying force to the actuating arm 128, the clamp body 112 deforms from its resting state as depicted in FIGS. 2A, 13A, and 7A. Such a deformation results in the mouth of the clamp 100 (i.e., the edge 124 where the first surface 114 and the second surface 118 contact) opening. With the mouth open the clamp body 112 can be placed around the tissue bundle 132. Pressure can then be released, resulting in the clamp body 112 returning to its resting shape, thereby encasing the tissue bundle 132 with the vessel 134 inside as depicted in FIGS. 1, 3, and 7C.

As outlined above, the actuating arm 128 is then rotated through the first aperture 410 of the first surface 114 to compress the tissue bundle 132 between the actuating arm 128 and the second surface 118. In instances where the width of the first aperture 410 is less than the width of the actuating arm 128, the actuating arm 128 can be resiliently biased in a direction substantially perpendicular to the axis of rotation. As a result, force can be applied to reduce the width of the actuating arm 128 to permit it to pass through the narrower first aperture 410. Once the actuating arm 128 passes through the first aperture 410, the force perpendicular to the axis of rotation of the actuating arm 128 can be removed, thereby allowing the actuating arm 128 to return to its original width.

The actuating arm 128 can be a solid piece of material, multiple pieces of material that form a substantially solid surface, or an outline with an internal aperture (e.g., a bent wire). If a wire is used, it will need to have a large enough gauge so as to prevent it, when ratcheted down, from cutting into the tissue bundle 132.

To reduce the amount of force required to open the mouth of the clamp 100, the second actuating arm 714 can be attached to the second surface 118. To provide for such a lever structure, the length of the actuating arm(s) 128, 714 will be at least longer than the clamp body 112.

The actuating arm 128 should be able to be rotated forward (i.e., away from the second surface 118), permitting the actuating arm 128 to be placed in front of the clamp body 112 during insertion. This will allow for a reduced height profile of the clamp 100 during insertion thereby necessitating smaller incisions during surgical procedures.

The clamp 100 has at least two apertures which permit the actuating arm 128 to pass through the first surface 114 and compress the tissue bundle 132 against the second surface 118. The first aperture 410 is located in the first surface 114 and the second aperture 412 is located in the connecting surface 120. To permit the actuating arm 128 to open and close the mouth of the clamp 100, the first aperture 410 is narrower than the actuating arm 128. Furthermore, the second aperture 412 can have a ratchet component described below. The second aperture 412 need not extend entirely through the connecting surface 120. Indeed, in some embodiments, the second aperture 412 may only extend partway down the connecting surface 120, thereby leaving a lip 310 at the junction 122 of the second surface 118 and the connecting surface 120. The bundle of tissue 132, including the vessel 134, can then be compressed against not only the second surface 118 and the actuating arm 128, but the lip 310 as well. This lip 310 permits compression of the bundle of tissue 132, including the vessel 134, from all sides (i.e., the actuating arm 128 compresses the bundle of tissue 132, including the vessel 134, against both the second surface 118 and the lip 310).

Just as a clamp body 112 containing more than three surfaces is outlined in the present disclosure, a clamp body 112 containing more than two apertures is envisioned. Indeed, the number of apertures can be equal to one less than the number of surfaces. For example, a hexagon-shaped clamp body 112 can contain up to five apertures with the actuating arm 128 compressing the bundle of tissue 132, including the vessel 134, against the sixth surface that does not have an aperture. It will be understood that more than one of the apertures can comprise a ratchet component when paired with the actuating arm 128. Furthermore, each surface is not required to have an aperture. Referencing the hexagon-shaped clamp 100 discussed above, in other embodiments, the clamp body 112 can contain four apertures. In these embodiments, the sixth surface acts as the surface the vessel 134 is compressed against and the fifth surface acts as a lip 310 that provides a secondary surface against which the bundle of tissue 132, including the vessel 134, may be compressed. These embodiments permit the bundle of tissue 132, including the vessel 134, to be compressed from all sides. In some embodiments, the compression from all sides may be uniform (i.e., the actuating arm 128 applies the same compression force against the second surface 118 as it does against the lip 310). In other embodiments the compression from all sides is not uniform (e.g., the actuating arm 128 applies a stronger compression force against the second surface 118 than the lip 310).

In some embodiments, the ratchet component is formed by the outer edge of an aperture comprising a linear rack of teeth 130 combined with the actuating arm 128 acting as a pawl (or click) 610 that engages the teeth 130. In other embodiments, the hinge 126 may include a ratchet component. Specifically, the hinge 126 may contain a pawl 810 that works in conjunction with teeth 812 on the actuating arm 128.

Figure 9:
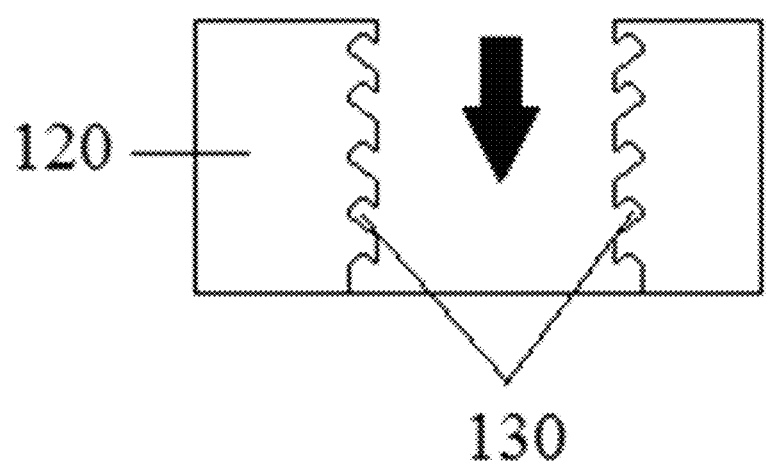
FIG. 9 shows one embodiment of a side in the surgical clamp which incorporates linear teeth as part of the ratchet component.

In some embodiments, the teeth 130 are uniform but asymmetrical, with each tooth having a moderate slope on one edge and a much steeper slope on the other edge as depicted in FIG. 9. When the actuating arm 128 is moving in the unrestricted direction (i.e., rotating towards the second surface 118), the actuating arm 128 or pawl easily slides up and over the gently sloped edges of the teeth 130. A spring force then forces the actuating arm 128 (sometimes with an audible "click") into the depression between the teeth 130 as it passes the tip of each tooth 130. When the actuating arm 128 moves in the opposite direction (i.e., away from the second surface 118), however, the actuating arm 128 or pawl will catch against the steeply sloped edge of the first tooth 130 it encounters, thereby locking it against the tooth 130 and preventing any further motion in that direction. Such a ratcheting mechanism permits the tension to be dynamically applied to the tissue bundle 132 containing the vessel 134. Furthermore, the teeth 130 need not be sloped, but may be curved as depicted in FIG. 9. Regardless of whether the ratchet component is part of the aperture and/or part of the hinge 126, such a ratchet component will be reversible such that the user can directly or indirectly apply a force to an element of the mechanism (e.g., the pawl 810 or the actuating arm 128) to permit the actuating arm 128 to rotate away from the second surface 118, which does not contain an aperture. In some embodiments, the spring force applied to the actuating arm 128 is the result of the actuating arm 128 being resiliently biased in a direction substantially perpendicular to the axis of rotation. This permits the user to disengage the ratchet component by compressing the actuating arm 128 into the center of the aperture and rotating the actuating arm 128 away from the second surface 118.

In any of the embodiments described herein, any of the edges described herein can be rounded or curved so as to not provide a sharp edge that may be harmful to a patient. In some embodiments, one or more of the components of the tensionable surgical clamps described herein can be covered with a protective coating such as, for example, a polymer. In some embodiments, one or more of the components of the tensionable surgical clamps described herein can be covered with a protective coating such as, for example, an antibacterial coating or anti-inflammatory coating.

Figure 7D:
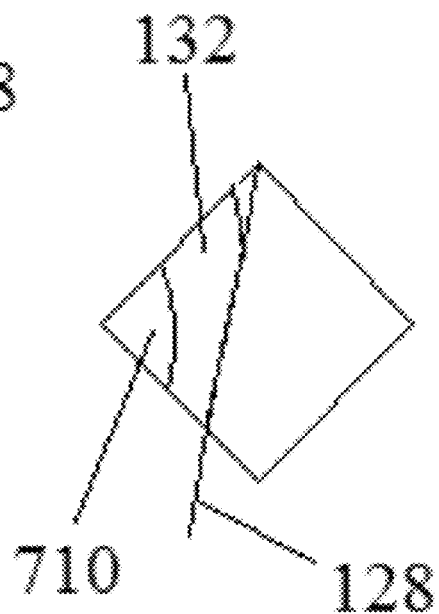
FIG. 7D shows a side view of one four-sided embodiment of the surgical clamp with the vessel under compression from both the balloon and the actuating arm.
Figure 8:
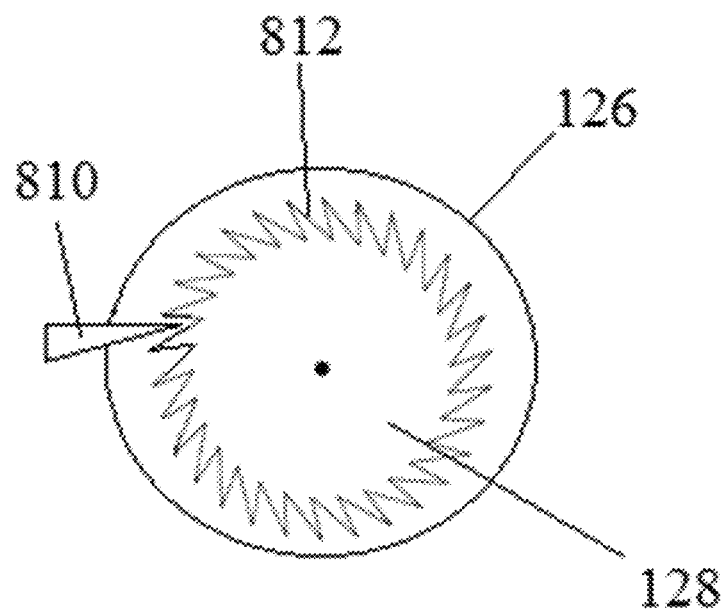
FIG. 8 shows a side view of one embodiment of a hinge in the surgical clamp which incorporates a ratchet component.
Figure 11A:
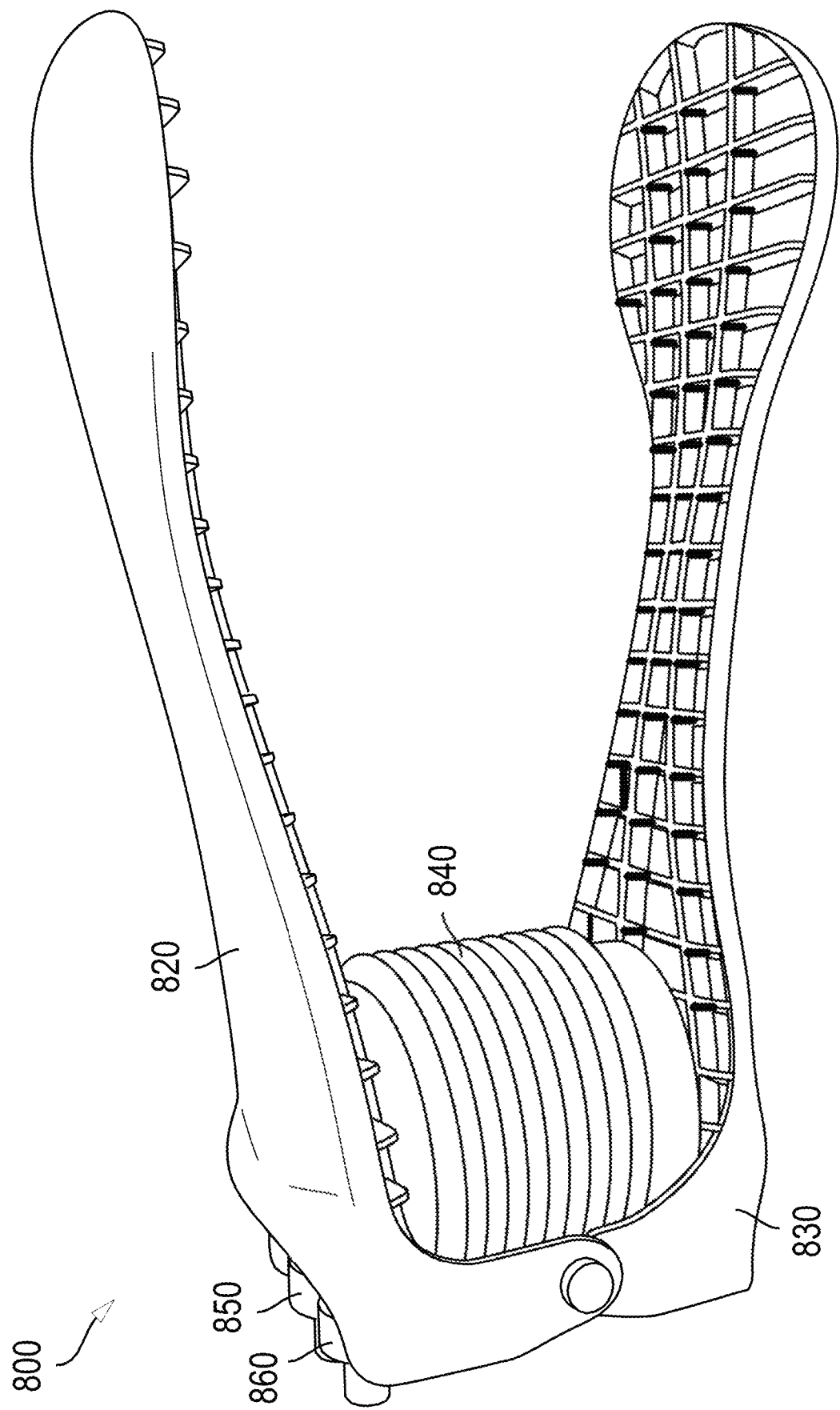
FIG. 11A shows one embodiment of a pump in the open position.
Figure 11B:
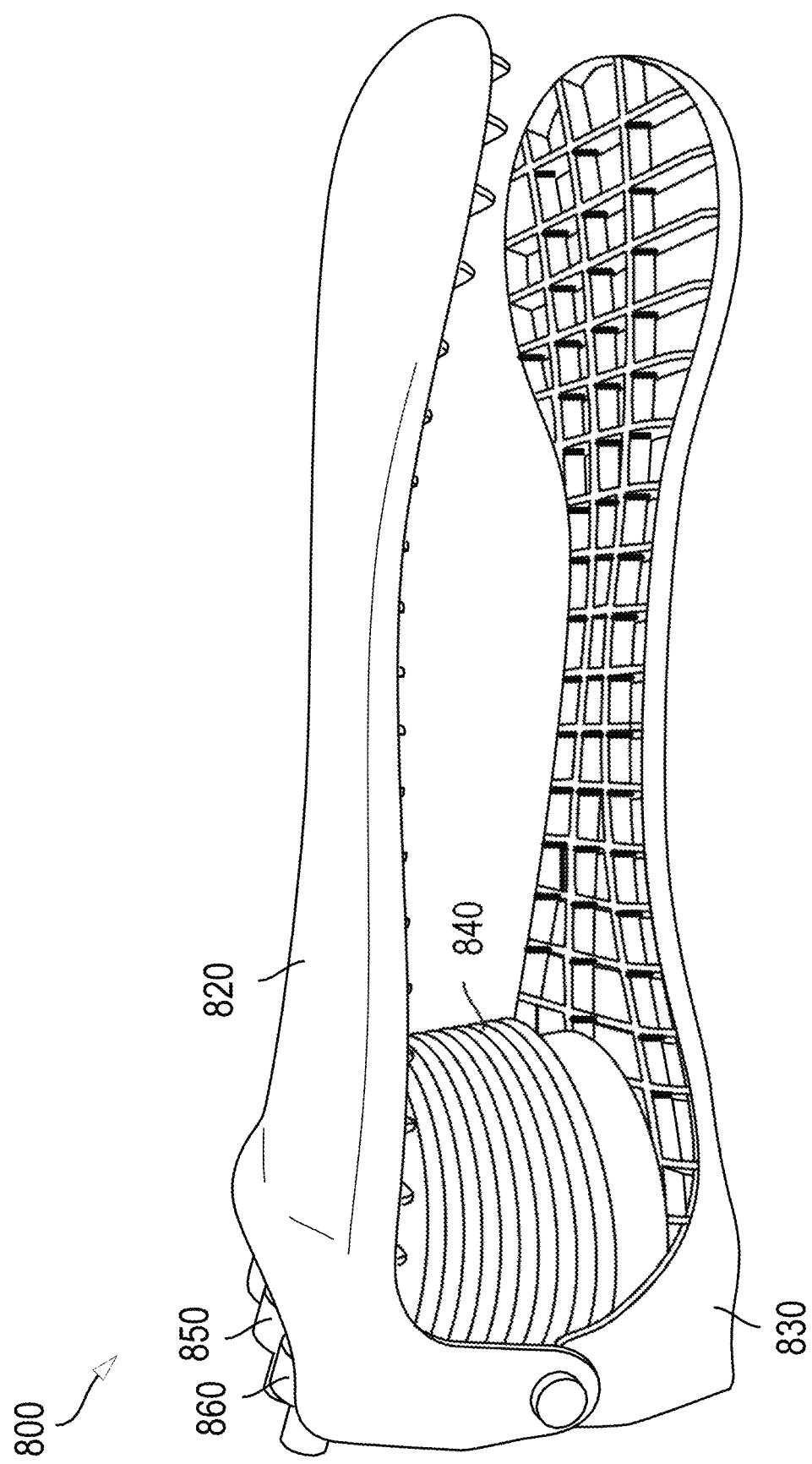
FIG. 11B shows the embodiment of the pump depicted in FIG. 11A but in the closed position.

To further assist with compression of the tissue bundle 132, an inflatable balloon 710 can be attached to the interior of the clamp body 112. The balloon 710 can be inflated by the user to further compress the tissue bundle 132, including the vessel 134, as depicted in FIG. 7D. In some embodiments, the inflatable balloon 710 can be inflated by a pump 800. A representative pump is depicted in FIGS. 11A and 11B. Referring to FIGS. 11A and 11B, the pump 800 comprises two pivoting members 820 and 830, encompassing a billow 840. Upon compression of the two pivoting members 820 and 830 towards each other, the billow 840 is compressed and forces air out an export terminal 850 through a connection hose (not shown) to the balloon 710. Upon releasing the two pivoting members 820 and 830, such that they move away from one another, the billow 840 is expanded and draws air in from an import terminal 860, thus refilling the billow 840.

Figure 10:
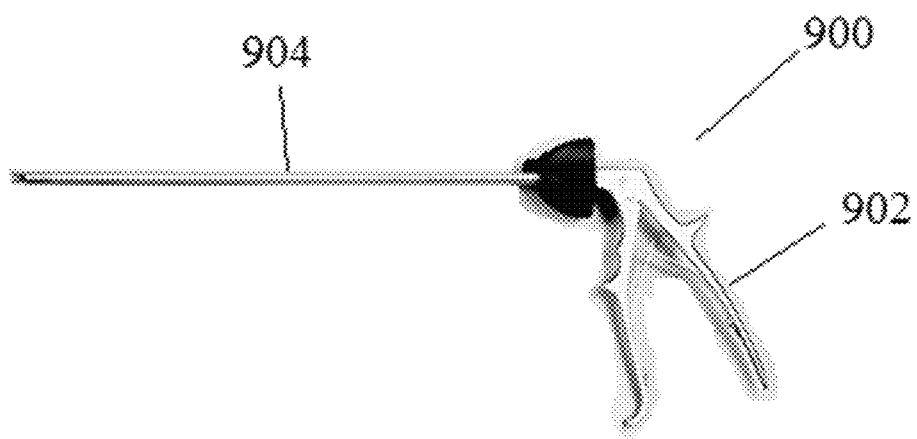
FIG. 10 shows one embodiment of an applicator used in connection with the surgical clamp.

For certain procedures, the disclosed clamp 100 will be applied with an applicator 900. The applicator 900 may be an elongated tool comprising a handle 902 and an arm 904. The handle 902 permits the user to manipulate the applicator 900. The arm 904 engages the clamp 100 and can apply the necessary force to the clamp 100 to open the mouth of the clamp 100 to permit the clamp body 112 to encircle the tissue bundle 132, including the vessel 134, or be removed from the surgical area. One example of an applicator 900 is depicted in FIG. 10. The applicator 900 may also be used to assist with ratcheting or releasing the actuating arm 128. The applicator 900 may be further attached to the balloon 710, thereby permitting the surgeon to inflate or deflate the balloon 710 as necessary.

The disclosed applicator 900 may be removable. Specifically, the applicator 900 can be temporarily attached to at least one anchor point 712 of the clamp 100. The anchor point(s) 712 can be located on the actuating arm 128. The anchor point(s) 712 can be located on the clamp body 112. In some embodiments, the anchor point(s) 712 are located on the side of the body 112 that does not contain an aperture. In this configuration, the applicator 900 may act as a second actuating arm 128 to provide the leverage required to open the mouth of the clamp 100 to permit the tissue bundle 132 containing the vessel 134 to be encircled. Once the clamp 100 is positioned, the applicator 900 may be removed. The removal of the applicator 900 can provide additional room for the surgeon to operate.

It will be understood that the clamp 100 can be constructed of any material which can be sterilized for surgical use including, but not limited to, stainless steel, chrome, titanium, vanadium, plastics, and polymer composites, or any combinations thereof. The clamp materials used may render the clamp 100 disposable. Specifically, the disclosed clamp 100 may be capable of being sterilized only prior to initial use. In addition, the clamp materials used may reusable (i.e., capable of being sterilized after initial use). To assist with such sterilization, the actuating arm 128 may be removably attached to the body 112, thereby permitting the actuating arm 128 to be separated from the body 112. Such separation may assist with sterilization.

Certain embodiments of a tensionable surgical clamp have been described herein. It is to be understood that other embodiments and variations can be devised by others skilled in the art without departing from the spirit and scope of the claimed subject matter. All such modifications and other embodiments are intended to be within the scope of the above description and in the following claims.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A surgical clamp comprising:
   a clamp body having a first surface containing a first aperture, a second surface, and a connecting surface containing a second aperture, wherein the clamp body is resiliently biased such that the first surface and the second surface contact each other at an edge;
   a hinge located at the edge;
   an actuating arm, rotatably secured to the first surface by the hinge, wherein the actuating arm in conjunction with at least one other element of the surgical clamp comprises a ratchet component; and
   a latching mechanism secured to the first surface and second surface at the edge;
   wherein the first aperture and second aperture are configured to permit the actuating arm to rotate through planes of the first surface and the connecting surface.

2. The surgical clamp of claim 1, wherein the clamp body is comprised of more than three surfaces.

3. The surgical clamp of claim 2, wherein the clamp body includes more than two apertures.

4. The surgical clamp of claim 1, wherein at least one of the first surface, second surface, or connecting surface is curved.

5. The surgical clamp of claim 4, wherein the clamp body is substantially circular in shape.

6. The surgical clamp of claim 1, further comprising a second hinge secured to the second surface.

7. The surgical clamp of claim 6, further comprising a second actuating arm secured to the second surface by the second hinge.

8. The surgical clamp of claim 1, wherein the actuating arm is resiliently biased such that the width of the actuating arm can be reduced by compression.

9. The surgical clamp of claim 1, wherein the actuating arm comprises a bent wire.

10. The surgical clamp of claim 1, wherein the outer edge of the second aperture includes a linear rack of teeth and the ratchet component comprises the linear rack of teeth in combination with the actuating arm acting as a pawl.

11. The surgical clamp of claim 1, wherein the hinge includes a pawl component, the outer edge of the actuating arm includes teeth, and the ratchet component comprises the teeth in combination with the pawl component.

12. The surgical clamp of claim 1, further comprising an inflatable balloon secured to the second surface on the interior of the clamp body.

13. The surgical clamp of claim 12, further comprising a pump connected to the inflatable balloon.

14. The surgical clamp of claim 1, wherein the surgical clamp is constructed of material consisting of stainless steel, titanium, plastic, polymer composites or any combinations thereof.

\* \* \* \* \*